Figure 1:
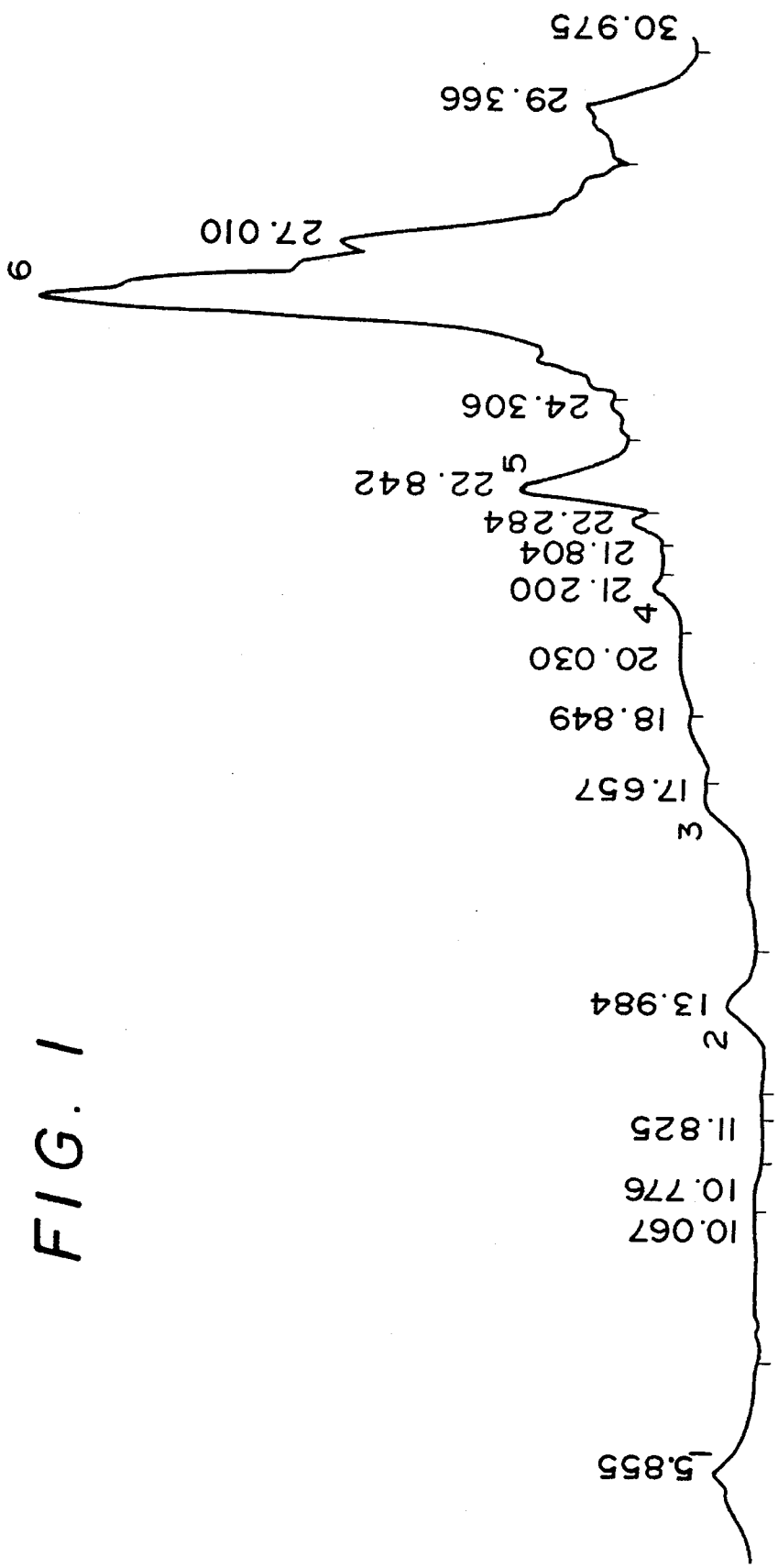
Figure 2:
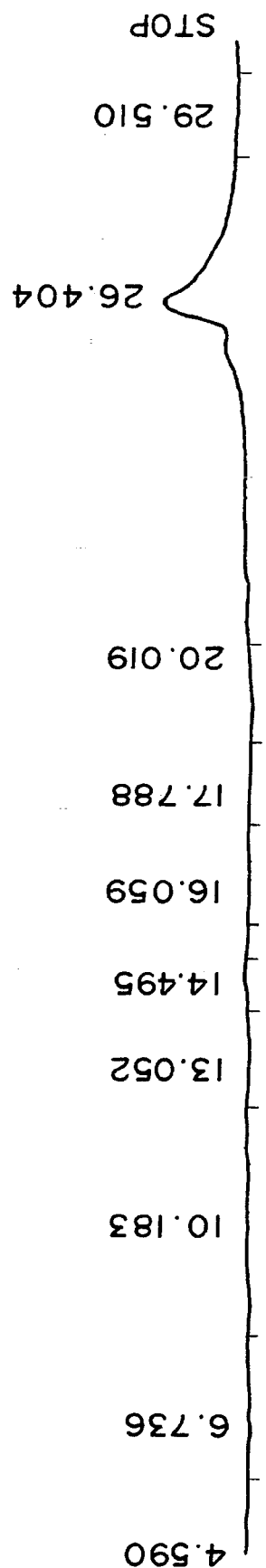
Figure 3:

United States Patent [19]

Lipps et al.

[11] Patent Number: 5,576,297
[45] Date of Patent: Nov. 19, 1996

[54] EMBODIMENTS OF NATURAL AND SYNTHETIC LETHAL TOXIN NEUTRALIZING FACTORS AND THEIR UTILITY AS TREATMENT FOR ENVENOMATION

[76] Inventors: Binie V. Lipps; Frederick W. Lipps, both of 4509 Mimosa Dr., Bellaire, Tex. 77401

[21] Appl. No.: 310,340

[22] Filed: Sep. 22, 1994

Related U.S. Application Data

[63] Continuation-in-part of Ser. No. 58,387, May 10, 1993, abandoned.

[51] Int. Cl.$^6$ .......................... A61K 38/10; A61K 38/16; C07K 7/08; C07K 14/47
[52] U.S. Cl. .................. 514/14; 514/12; 514/21; 530/326; 530/350; 530/362; 530/380; 530/416; 530/829; 530/856
[58] Field of Search .................................. 514/8, 12, 21, 514/14; 530/350, 326, 362, 363, 364, 380, 412, 416, 829, 830, 856

[56] References Cited

PUBLICATIONS

Bone "The Pathogenesis of Sepsis" Ann Int Med 115(6) 457–469 1991.
Guyton "Textbook of Medical Physiology" 8th Ed 269–271 1991.
Mousstaché et al "Mechanisms of Resistance of the Opossum to Some Snake Venoms" Toxicon 17(Suppl. 1) 130 1979.
Domont et al. "Natural Anti–Snake Venom Proteins" Toxicon 29(10) 1183–1194 1991.
Perales et al "Neutralization of the Oedematogenic activity of Bothrops Jararaca venom on the Mouse Paw by an antibothropic Fraction Isolated from Opossum serum" Agents Actions 37(3–4) 250–259 1992.
Tomihara et al. "Purification of Three Antihemorrhagic Factors From The Serum of A Mongoose" Toxicon 25(6) 685–689 1987.
Perates et al. "Anti Snake Venom Protein from Didelphidae" Abstract 10th World Congress. Toxicon 30(5–6) 543 1992.
Menchaca et al. "The Purification & Characterization of An Antihemerrhagic Factor in Opossum Serum" Toxicon 19(5) 623–632 1981.

*Primary Examiner*—Mindy Fleisher
*Assistant Examiner*—Nancy J. Degen
*Attorney, Agent, or Firm*—John R. Casperson

[57] ABSTRACT

Opossum whole serum exhibits a life saving property by neutralizing the lethality of venoms from all major families of poisonous snakes, and therefore an injection of Opossum serum can used as a novel treatment for many types of envenomation. Preferably, the injectable treatment for envenomation should be a composition obtained from the fraction of Opossum whole serum which contains the lethal toxin neutralizing factor, i.e. the so called "natural LTNF", in purity. A method is given for the manufacture of a lethal toxin neutralizing factor from the serum of an opossum (*Didelphis virginiana*) serum, by fractionating the opossum serum and isolating this select fraction from the plurality of fractions having an N terminal amino acid sequence given by SEQ ID No: 1. A short peptide was synthesized having SEQ ID No: 1. The synthetic peptide having sequence SEQ ID No: 1 shows lethal toxin neutralizing activity similar to the natural LTNF from opossum or mongoose sera. The synthetic LTNF also has life saving utility.

11 Claims, 3 Drawing Sheets

1 2 3 4

5,576,297

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 15
        ( B ) TYPE: AMINO ACID
        ( C ) STRANDEDNESS: SINGLE
        ( D ) TOPOLOGY: LINEAR ( i i ) MOLECULE TYPE: PROTEIN IN SEQ ID NO: 1

( i i i ) HYPOTHETICAL: NO ( i v ) ANTI-SENSE: NO ( v ) FRAGMENT TYPE: N ( v i ) ORIGINAL SOURCE: OPOSSUM SERA: SEQ ID NO: 1:
        ( A ) ORGANISM: DIDELPHIS VIRINIANA
        ( B ) STRAIN: WILD
        ( C ) INDIVIDUAL ISOLATE: TEXAS WILD
        ( D ) DEVELOPMENTAL STAGE: ADULT
        ( E ) HAPLOTYPE:
        ( F ) TISSUE TYPE: BLOOD
        ( G ) CELL TYPE:
        ( H ) CELL LINE:
        ( I ) ORGANELLE:

( v i i ) IMMEDIATE SOURCE: OPOSSUM SERA SEQ ID NO: 1:
        ( A ) LIBRARY:
        ( B ) CLONE:

( x ) PUBLICATION INFORMATION:
        ( A ) AUTHORS: JONAS PERALES, ET AL.
        ( B ) TITLE: ANTI-SNAKE VENOM FORM DIDELPHIDAE
        ( C ) JOURNAL: INTERNATIONAL SOCIETY ON
            TOXINOLOGY
        ( D ) VOLUME: 10TH WORLD CONGRESS ON ANIMAL
            PLANT AND MICROBIAL TOXINS 3-8 NOV 1991,
            SINGAPORE
        ( E ) ISSUE: PROGRAMME AND ABSTRACTS
        ( F ) PAGES: 104

(G) DATE: 3-8 NOV 1991

(xi) SEQUENCE DESCRIPTION: SEQ ID NO: 1:

Leu Lys Ala Met Asp Pro Thr Pro Pro Leu
              5                       10
Trp Ile Lys Thr Glu
              15

EMBODIMENTS OF NATURAL AND SYNTHETIC LETHAL TOXIN NEUTRALIZING FACTORS AND THEIR UTILITY AS TREATMENT FOR ENVENOMATION

SPECIFICATION

This application is a continuation in part of the application Ser. No. 08/058,387, filed May 10, 1993, now abandoned.

TECHNICAL FIELD

The present invention embodies a treatment for diverse envenomation and intoxication to be used in life saving applications. More particularly, the present invention relates to a molecular moiety called "lethal toxin neutralizing factor" for the treatment of venomous snake bites.

BACKGROUND OF THE INVENTION

Several warm-blooded animals, such as opossums, mongoose, meerkats, wood rats and cotton rats have shown a remarkable resistance to the toxic action of snake venoms (1, 2 and 3). An antihemorrhagic factor in serum of Sigmodon hispidus (cotton rat), has been isolated and characterized (4). This antihemorrhagic factor has physical properties different from the immunoglobulins of serum. An antihemorrhagic factor has also been isolated, purified and characterized from opossum serum (5, 6 and 7). The opossum serum derived antihemorrhagic factor has an isoelectric pH 4.1 and molecular weight 68,000 daltons. According to the art of the published work, the antihemorrhagic factor in the serum of opossum is albumin or closely associated with albumin. However, these investigators did not claim the utility of antihemorragic factor as a treatment for snakebite, nor did they measure its neutralizing activity versus venom toxins except for observing its effect on skin hemorrhage.

This invention relates to: (1) the lethal toxin neutralizing effect of opossum serum; (2) a purified component from opossum serum having lethal toxin neutralizing activity; and (3) a synthetic peptide having similar lethal toxin neutralizing activity for crude venoms of various species of snakes containing diverse deadly toxins acting in different physiological ways. All three: opossum serum; the purified fraction from opossum serum; and the synthetic peptide of the purified fraction provide relatively universal treatment for snakebite. All three neutralize venoms from the major families of poisonous snakes, and therefore, provide a replacement for antivenoms made in horses.

Currently, antivenoms produced in horses provide the only available treatment for snakebite, in spite of the fact that some people are hypersensitive to horse proteins. Antivenom treatment for snakebite has been in practice for over forty years without much improvement. The only consideration being, that antivenoms for snake species prevalent to the region be available, and that the correct antivenom should be used. In order to administer the proper specific antivenom, the victim or physician must identify the guilty snake, which is impossible in many cases. Numerous antivenoms now exist worldwide, which are mostly made in horse, although a few are made in goats. It would be desirable to find combinations of venoms giving a broad spectrum of protective antibodies, but this has not yet happened.

Treatment of snakebite would be greatly enhanced, if a drug could be found which would overcome the problems associated with antivenoms. A drug which will neutralize the toxicity of venoms from all major species will be a breakthrough.

REFERENCES CITED

U.S. Patent

1. U.S. Pat. No. 4/012,502 Mar. 15, 1977 Van B. Philpot, Jr.

OTHER PUBLICATIONS

0. Kilman J A, Toxicon 14:337–340 (1976).

1. Ovadia M and Kochava E, Toxicon 15:54 (1977).

2. Werner, R M and Vick J A, Toxicon 15:29 (1977).

3. Perez J, Haws W, Garcia V and Jennings B, Toxicon 16:375 (1979).

4. Pichyangkul S and Perez J C, Toxicon 19:205 (1981)

5. Menchaca J M and Perez J C, Toxicon 19:623 (1981).

6. ibid., pages 623–632.

7. Tomihara Yet al., Toxicon 25(6): 685–689 (1987).

8. Perales J, Toxicon 30 (5–6): 543 (1992). 9. Catanese J J and Kress L F, Biochemistry 31: 410–418 (1992)

OBJECTS OF THE INVENTION

It is an object of the present invention to provide a composition consisting of a natural lethal toxin neutralizing factor (LTNF) derived from opossum serum that serves as a relatively universal treatment for snakebite. Said lethal toxin neutralizing factor being an effective life saving treatment for snakebite for a large variety of snakes having diverse type of lethal activities. It is a further object of the present invention to provide a lethal toxin neutralizing factor that does not include horse proteins.

It is also an object of the present invention to provide a short synthetic peptide which also has activity as a lethal toxin neutralizing factor with the same or similar utility as the naturally occurring product. It is believed that the use of both natural and synthetic LTNF can be extended to treat sepsis, allergy etc. and other nonspecific disorders caused by environment.

Thus, both embodiments of the present invention, i.e. natural and synthetic LTNF, can become alternative treatments for various snakebites requiring extremely low concentrations of protein; and it is believed that their use can be extended to treat scorpion and bee stings, and also toxins from plats, bacteria, etc. It is further believed that this invention has military applications due to the variety of unknown exposures that can occur under military conditions.

Both natural and synthetic LTNF should be given intravenously in a manner similar to an antivenom treatment to give a systemic effect rather than given topically or by perfusing the bite-wound to give a localized effect such as antihemorrhage. –

BRIEF DESCRIPTION OF THE DRAWINGS

Drawing 1 shows the high pressure liquid chromatography profile of opossum serum using an anion exchange column. Peak number six represents the lethal toxin neutralizing factor, LTNF.

Drawing 2 shows the high pressure liquid chromatography profile of a concentrate from fraction number six showing a single peak of pure natural LTNF.

Drawing 3 shows the electrophoretic profile of opossum serum and purified natural LTNF on a 14% Novex gel with markers. The molecular weight of natural LTNF corresponds to the albumin component of the opossum serum and the marker bovine serum albumin, which is approximately 68,000 daltons.

SUMMARY OF THE INVENTION

The present invention is a method of producing a naturally occurring and a synthetic lethal toxin neutralizing factor having utility as a life saving agent for use with diverse venoms and toxins. The naturally occurring factor requires: (1) obtaining opossum serum; (2) fractionating the opossum serum into a plurality of fractions; (3) identifying and isolating the fraction having the lethal toxin neutralizing activity for venoms from the major families of poisonous snakes. The synthetic factor requires: (1) Amino acid sequencing of the purified LTNF from opossum serum; and (2) synthesizing a short peptide of fifteen amino acids, which is identical to the first 15 N terminal amino acids of the naturally occurring factor from opossum serum. The synthetic lethal toxin neutralizing factor and the first 15 N-terminal amino acids of the naturally occurring factor have the sequence:

Leu-Lys-Ala-Met-Asp-Pro-Thr-Pro-Pro-Leu-Trp-Ile-Lys-Thr-Glu, which will be referred to as SEQ ID No:1.

The purification of the naturally occurring lethal toxin neutralizing factor includes fractionating the opossum serum on an anion exchange column of a liquid phase fractionating system. This liquid phase fractionating system is a high pressure liquid chromatography system. The fractions of the opossum serum are eluted with a buffer material. This buffer material is an aqueous gradient Trizma-HCl buffer having the pH 7.4 and molarity in the gradient range of 0.01 molar to 1.0 molar.

The eluted fractions of opossum serum are dialyzed against distilled water as to remove the buffer chemicals. Initially, all fractions were tested for the lethal toxin neutralizing activity and the one fraction having such activity is called the lethal toxin neutralizing factor, "LTNF". This is a reproducible procedure and the same fraction always has the lethal toxin neutralizing activity for various venoms.

Lethality of venom can be due to several types of toxins present in the venom which exert different physiological effects, such as respiratory failure, blood clotting, muscular paralysis, cardiac arrest, cell lysis and hemorrhage; whereas, hemorrhage is only one of many causes of death due to envenomation. The lethal toxin neutralizing factor exhibits the ability to neutralize all effects associated with the lethality of snake venom toxins in mice. The lethal toxin neutralizing factor of the present invention shows inhibition or neutralization of toxins from the venoms of major families of snakes. The molecular weight of the opossum derived lethal toxin neutralizing factor is about 68 kDa. The sequence of the first fifteen amino acids from the N terminal is SEQ ID No: 1.

The synthesized peptide having the first fifteen amino acid sequence from the N terminal shows similar neutralization activity for toxins from venoms when tested in mice. An extremely low concentration of this lethal toxin neutralizing factor is required to neutralize the lethal effect of snake venoms in comparison to the protein concentration required using currently available antivenom. Thus, both compositions of the present invention natural and synthetic LTNF can become alternative treatments for various snakebites and it is believed that their use can be extended to treat scorpion and bee stings, including toxins from plants, bacteria, etc.

BRIEF DESCRIPTION OF THE DRAWINGS

Drawing 1 shows the high pressure liquid chromtography profile of opossum serum using an anion exchange column. Peak number six represents the toxin neuralizing factor, LTNF.

Drawing 2 shows the high pressure liquid chromatography profile of a concentrate from fraction number six showing a simgle peak of pure natural LTNF.

Drawing 3 shows the electrophoretic profile of opossum serum and purifiled natural LTNF ona 14% Novex gel with markers. The molecular weight of nature LTNF corresponds to the albumin cmponent of the opossum and the marker bovine serum albumin, which is approximately 68,00 daltons.

DETAILED DESCRIPTION OF THE INVENTION

Whole sera from opossum and mongoose were tested for their neutralizing property versus several snake venoms belonging to four major families of poisonous snakes: Crotalidae, Elapidae Hydrolidae and Viperidae. The following sample of venoms were tested:

| | |
|---|---|
| *Crotalus adamanteus,* | Family Crotalidae |
| *Crotalus atrox* | Family Crotalidae |
| *Naja n. atra* | Family Elapidae |
| *Naja n. kaouthia* | Family Elapidae |
| *Vipera russellii* | Family Viperidae |
| *Oxyuranus scutellatus* | Family Elapidae |
| Sea Snake | Family Hydrolidae |

In order to measure the inhibition of toxicity, mice were injected with a predetermined lethal dose of the respective venoms in 0.1 ml volume intraperitoneally. Immediately, the control mice were injected with 0.5 ml 0.05M phosphate buffer saline (PBS) and the experimental with same volume of opossum or mongoose serum. For each experimental category, three (3) mice were used.

TABLE I

NEUTRALIZATION OF LETHAL EFFECTS OF SNAKE VENOMS BY OPOSSUM SERUM IN MICE

| | Death/Survival | |
|---|---|---|
| Venom | Opossum Serum | Control |
| *Crotalus adamanteus* | 0/3 | 3/0 |
| *Crotalus atrox* | 0/3 | 3/0 |
| *Naja n. atra* | 0/3 | 3/0 |
| *Naja n. kaouthia* | 0/3 | 3/0 |
| *Vipera russellii* | 0/3 | 3/0 |
| *Oxyuranus s. scutellatus* | 0/3 | 3/0 |
| Sea Snake | 0/3 | 3/0 |

The results of Table I clearly show that opossum serum is rendering protection against lethal doses of various snake venoms from all families of poisonous snakes. The mice in controls died within 24 hours. As little as 0.5 ml of opossum serum is adequate to cause neutralization and render protection from the envenomation which otherwise would be lethal.

Opossum and mongoose sera were fractionated into immunoglobulin and albumin components by saturated ammonium sulfate treatment. The precipitated immunoglobulin component was dissolved in 0.05M PBS to the starting volume of the serum. After dialysis, both albumin and immunoglobulin components were tested versus lethal doses of various snake venoms. The mice were injected with predetermined lethal doses of snake venoms followed by inoculation with 0.5 ml of albumin or immunoglobulin components. The results are presented in table II.

TABLE II

NEUTRALIZATION OF LETHAL EFFECTS OF SNAKE VENOMS IN MICE BY OPOSSUM SERUM ALBUMIN COMPONENT

| Venom | Death/Survival | |
|---|---|---|
| | Albumin Component | Immnoglobulin component |
| C. atrox | 0/3 | 3/0 |
| N. n. kaouthia | 0/3 | 3/0 |
| V. russellii | 0/3 | 3/0 |

The results of the Table II clearly show that the protective factor resides in the albumin component of the opossum serum for the venoms of *C. atrox, N.n. kaouthia* and *V. russellii*. Thus, the neutralization of the toxic effects of venoms is not due to antigen antibody reaction.

Opossum serum was fractionated on a liquid phase fractionating system. Specifically, using a high pressure liquid chromatography (HPLC), from Toso Co. Japan and anion exchange column (Type PL-SAX Q 1125, with 10μ particles, 1000 Å pores and column dimensions 150×10 mm) from Polymer Laboratories UK, maintained at 20° C. temperature. Approximately 25 mg of serum protein was loaded into the column to fractionate. The elution was accomplished with gradient Trizma-HCl buffer having pH 7.4 and molarity gradient in the range 0.01M to 1.0M. Nine different fractions were obtained which were individually pooled from several HPLC runs (Drawing no. 1). All fractions were dialyzed and concentrated using Spectrum dialysis apparatus. The protein concentration for each fraction was measured on spectrophotometer using protein assay kit from Bio-Rad company. Each fraction was adjusted to 1 mg/ml concentration of the protein content. Each fraction was mixed with an equal volume lethal dose of venom from *C. atrox*. In this case, 100 μg of the protein from each fraction was tested versus a predetermined lethal dose of *C. atrox* venom.

TABLE III

IDENTIFICATION OF VENOM NEUTRALIZING FACTOR FROM OPOSSUM SERUM

| Fraction # | Death/Survival |
|---|---|
| 1 | 3/0 |
| 2 | 3/0 |
| 3 | 3/0 |
| 4 | 3/0 |
| 5 | 3/0 |
| 6 | 0/3 |
| 7 | 3/0 |
| 8 | 3/0 |
| 9 | 3/0 |

The results of Table III show that the lethal toxin neutralizing factor resides in fraction number 6 of the nine different fractions for *C. atrox* venom.

One hundred micrograms of purified fraction no. 6, which is the lethal toxin neutralizing factor, natural LTNF, was mixed with an equal volume of the predetermined lethal doses of snake venoms to inject mice. The results are presented in table IV.

TABLE IV

NEUTRALIZATION EFFECT OF FRACTION 6 OF OPOSSUM SERUM

| Venoms | Death/Survival | |
|---|---|---|
| | Fraction 6 | Control |
| C. atrox | 0/3 | 3/0 |
| Vipera russellii | 0/3 | 3/0 |
| N. n. kaouthia | 0/3 | 3/0 |
| O. s. scutellatus | 0/3 | 3/0 |
| Sea Snake | 0/3 | 3/0 |

The fraction 6 is the natural LTNF showing ability to neutralize the toxic lethal effects of venoms of snakes from the major families. The fraction number six was concentrated and rerun on the HPLC under identical conditions of temperature, gradient buffer, etc. and it yielded one peak (Drawing no. 2). The material from this single peak was partially sequenced for its first fifteen amino acids of the N-terminal. Furthermore, a peptide for those fifteen amino acids was synthesized. The sequenced amino acids of N-terminal were identified as SEQ ID No: 1. The molecular weight of natural LTNF was determined by gel electrophoresis. The molecular weight of natural LTNF was reveled to be approximately 68,000 daltons corresponding to the albumin component of the opossum serum. The molecular weight of the synthetic LTNF is less than 6,000 daltons (Drawing no. 3).

The synthesized LTNF was tested with the venoms as documented in Table V. Mice were divided into three groups. Mice in groups I & II were injected with lethal doses of respective venoms. Immediately, the mice in group I were injected with 0.5 ml of PBS, while those in group II were injected with 500 μg of synthetic LTNF in 0.5 ml. Mice in group III were injected with 500 μg of synthetic LTNF and after 30 minutes they were given lethal doses of respective venoms. The results are presented in table V.

TABLE V

NEUTRALIZATION EFFECT OF SYNTHETIC LTNF

| Venoms | Death/Survival | | |
|---|---|---|---|
| | Group I (PBS Control) | Group II (LTNF Immediately) | Group III (LTNF ½ hr before) |
| C. atrox | 3/0 | 0/3 | 0/3 |
| N. n. kaouthia | 3/0 | 0/3 | 0/3 |
| V. russellil | 3/0 | 0/3 | 0/3 |
| O. scutellatus | 3/0 | 0/3 | 0/3 |
| Sea Snake | 3/0 | 0/3 | 0/3 |

The results of Table V clearly show the strong antilethal activity of synthetic LTNF, similar to the natural LTNF, which is identified in opossum serum. The lack of antigenic relationship between snake venom and opossum serum or LTNF, indicates that its activity is immunoglobulin independent. Therefore, the activity of synthetic LTNF, which is similar to the natural LTNF, may extend to other toxins, viruses, allergens, etc. The antilethal activity of synthetic LTNF was exhibited when it was administered ½ hour before the toxin injection, therefore, synthetic LTNF can be used as a preventive measure, especially for snake handlers, etc.

As was described previously, the opossum whole serum exhibits the property of neutralizing the lethality of venoms from major families of poisonous snakes. Because the neutralizing activity of opossum serum resides in the albumin component of the opossum serum, this neutralizing activity is not due to the antigen antibody reaction.

In the present invention, opossum serum was fractionated by high pressure liquid chromatography using an a anion exchange column. The procedure yielded nine different fractions. The lethal neutralizing factor was found in fraction number six (Drawing no. 1). This fraction showed the neutralization of snake venoms. Fraction 6 was concentrated and fractionated a second time on HPLC under identical conditions. The purified product gave a single peak in the HPLC profile (Drawing no. 2). The molecular weight of the purified material was 68 kDa as revealed by gel electrophoresis (Drawing no. 3).

One hundred micrograms of natural LTNF neutralized the lethal toxicity of a variety of venoms. The natural LTNF exhibits the sequence for its first fifteen amino acids as SEQ ID No: 1. The known sequence of the fifteen amino acids of natural LTNF was synthesized as a short peptide. Five hundred micrograms of the synthetic LTNF is capable of neutralizing lethal doses of venoms from snakes from major families. Moreover, the synthetic LTNF is immunogenic, since mice immunized with it were able to produce specific antibodies, which reacted with both natural and synthetic LTNF, thus proving its biological potency. The use of natural and synthetic LTNF can be expected to treat sepsis, allergies and other nonspecific disorders caused by the environment and as a preventive measure before possible exposure to various toxins.

The natural LTNF can be isolated from other species of opossums such as *Didelphis marsupialis, Philander opossum*, and *Lutreolina crassicaudata* and other animals like mongoose and meerkat.

The application of natural or synthetic LTNF, as treatment for snakebite, overcomes the problem of hypersensitivity occurring from the horse-derived antivenom.

The foregoing disclosure and description of the invention is illustrative and explanatory thereof. Various changes in the steps of the described method, or the details of the claim composition, can be made within the scope of the appended claims without departing from the true spirit of the invention.

---

We claim:

1. A method for treating a victim of envenomation, said method comprising injecting intravenously a composition into said victim, wherein said composition contains a lethal toxin neutralizing factor obtained from the sera of an opossum from the family Didelphis, wherein the victim has been envenomated by a bee.

2. A method for treating a victim of envenomation, said method comprising injecting intravenously a composition into said victim, wherein said composition contains a lethal toxin neutralizing factor obtained from the sera of an opossum from the family Didelphis, wherein the victim has been envenomated by a scorpion.

3. A method for treating a victim of a bacterial toxin said method comprising injecting intravenously a composition into said victim; wherein said composition comprises a lethal toxin neutralizing factor obtained from an animal having resistance to envenomation.

4. A method as in claim 3 wherein the animal is selected from the group consisting of *Didelphis marsupialis, Philander opossum*, and *Lutreolina crassicaudata* and the factor has a molecular weight of approximately 68,000 Daltons, and the first 15 amino acids from the N-terminus are identified in SEQ ID NO: 1.

5. A method for treating a victim of a plant toxin said method comprising injecting intravenously a composition into said victim; wherein said composition compromises a lethal toxin neutralizing factor obtained from an animal having resistance to envenomation.

6. A method as in claim 5 wherein the animal is selected from the group consisting of *Didelphis marsupialis, Philander opossum*, and *Lutreolina crassicaudata* and the factor has a molecular weight of approximately 68,000 Daltons, and the first 15 amino acids from the N-terminus are identified in SEQ ID NO: 1.

7. A method for treating a victim of envenomation, said method comprising injecting intravenously into said victim a lethal toxin neutralizing factor comprising a 15 amino acid peptide having a sequence given by SEQ ID NO: 1, wherein the victim is envenomated by a bee sting.

8. A method for treating a victim of envenomation, said method comprising injecting intravenously into said victim a lethal toxin neutralizing factor comprising a 15 amino acid peptide having a sequence given by SEQ ID NO: 1, wherein the victim is envenomated by a scorpion.

9. A method for treating a victim of a bee sting said method comprising applying topically to said victim a solution containing a lethal toxin neutralizing factor comprising a 15 amino acid peptide having a sequence given by SEQ ID NO: 1 at an area affected by the bee sting.

10. A method for treating a victim of a plant toxin said method comprising injecting intravenously into said victim a lethal toxin neutralizing factor comprising a 15 amino acid peptide having a sequence given by SEQ ID NO: 1.

11. A method for treating a victim of a bacterial toxin said method comprising injecting intravenously into said victim a solution containing a lethal toxin neutralizing factor comprising a 15 amino acid peptide having a sequence given by SEQ ID NO: 1.

* * * * *